United States Patent [19]

Stetter et al.

[11] Patent Number: 4,472,416
[45] Date of Patent: Sep. 18, 1984

[54] COMBATING FUNGI WITH SUBSTITUTED AZOLYL-PHENOXY DERIVATIVES

[75] Inventors: Jörg Stetter, Wuppertal; Karl H. Büchel, Burscheid; Paul-Ernst Frohberger, Leverkusen; Paul Reinecke, Leverkusen; Wilhelm Brandes, Leverkusen, all of Fed. Rep. of Germany

[73] Assignee: Bayer Aktiengesellschaft, Leverkusen, Fed. Rep. of Germany

[21] Appl. No.: 403,988

[22] Filed: Aug. 2, 1982

[30] Foreign Application Priority Data

Aug. 17, 1981 [DE] Fed. Rep. of Germany ....... 3132335

[51] Int. Cl.$^3$ .................. A01N 43/50; A01N 43/64; C07D 249/08; C07D 233/61
[52] U.S. Cl. ................................ 424/269; 424/245; 424/273 R; 548/101; 548/262; 548/341; 564/256
[58] Field of Search ............... 548/101, 262, 341; 424/269, 245, 273 R

[56] References Cited

U.S. PATENT DOCUMENTS 4,147,791  4/1979  Meiser et al. ................ 424/269

FOREIGN PATENT DOCUMENTS 2600799  7/1977  Fed. Rep. of Germany .
0001571  5/1979  Fed. Rep. of Germany .

*Primary Examiner*—Alton D. Rollins
*Attorney, Agent, or Firm*—Sprung, Horn, Kramer & Woods

[57] ABSTRACT

A substituted azolyl-phenoxy derivative of the formula $$(R^3O-N=C)_m \underset{X_n}{\underset{|}{\bigcirc}} \overset{R^2}{\underset{|}{-}} O-CH-B-R^1 \\ \underset{N}{\underset{\|}{|}} \overset{N}{\underset{A}{\diagdown}}$$

in which
A is a nitrogen atom or a CH group,
B is a keto group or a CH(OH) grouping,
$R^1$ is an alkyl or halogenoalkyl group of an optionally substituted aryl group,
$R^2$ is a hydrogen atom, an alkyl group or an optionally substituted phenyl group,
$R^3$ is a hydrogen atom, an alkyl, alkenyl or alkinyl group,
m is 1 or 2,
X is a halogen atom, or an alkyl, alkoxy, alkylthio, halogenoalkyl, halogenoalkoxy or halogenoalkylthio group, and
n is 0, 1 or 2, or an addition product thereof with an acid or metal salt, which possesses fungicidal activity particularly for combating cereal diseases as well as rust and scab diseases.

10 Claims, No Drawings

COMBATING FUNGI WITH SUBSTITUTED AZOLYL-PHENOXY DERIVATIVES

The present invention relates to certain new substituted azolyl-phenoxy derivatives, to several processes for their production and to their use as fungicides.

It has already been disclosed that 3,3-dimethyl-1-(imidazol-1-yl)- or -(1,2,4-triazol-1-yl)-1-yl)-1-phenoxybutan-2-ones and -ols which are substituted in the phenyl part exhibit in general good fungicidal properties (see U.S. Pat. No. 3,912,752, U.S. Pat. No. 3,952,002, U.S. Pat. No. 3,898,341, and U.S. Pat. No. 3,940,414). However, the action of these compounds is not always completely satisfactory in all fields of indication, in particular when low amounts and concentrations are used.

The present invention now provides, as new compounds, the substituted azolyl-phenoxy derivatives of the general formula

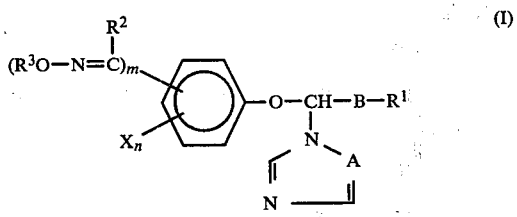

in which
A represents a nitrogen atom or a CH group,
B represents a keto group or a CH(OH) grouping,
$R^1$ represents an alkyl or halogenoalkyl group or an optionally substituted aryl group,
$R^2$ represents a hydrogen atom, an alkyl group or an optionally substituted phenyl group,
$R^3$ represents a hydrogen atom or an alkyl, alkenyl or alkinyl group,
m is 1 or 2,
X represents a halogen atom or an alkyl, alkoxy, alkylthio, halogenoalkyl, halogenoalkoxy or halogenoalkylthio group, and
n is 0, 1 or 2,
or the acid addition salts or metal salt complexes thereof.

The compounds of the formula (I) can be present in the syn or anti form; they occur predominantly as mixtures of the two forms.

Those compounds of the formula (I) in which B represents the CH(OH) grouping possess two asymmetric carbon atoms; they can therefore also be present as the two geometric isomers (threo and erythro form) which can occur in varying proportions. They are present as optical isomers in both cases. All isomers are claimed according to the invention.

According to the present invention we further provide a process for the production of a compound of the present invention, characterized in that (a) a halogenoether-ketone of the general formula

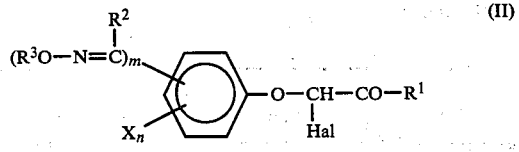

in which
$R^1$, $R^2$, $R^3$, X, m and n have the meanings given above, and
Hal represents a halogen atom,
is reacted, if desired after a prior reduction, where Hal represents a fluorine atom, with 1,2,4-triazole or imidazole, if appropriate in the presence of an acid-binding agent and, if appropriate, in the presence of a diluent, or (b) an azolylhalogenoketone of the general formula

in which
A and $R^1$ have the meanings given above, and
Hal' represents a halogen atom,
is reacted with a phenol of the general formula

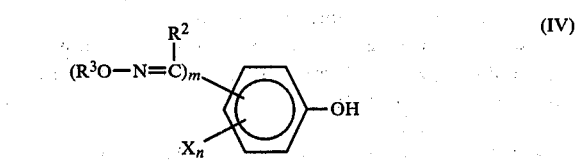

in which
$R^2$, $R^3$, X, m and n have the meanings given above, in the presence of an acid-binding agent and in the presence of a diluent, and (c), if a compound of formula (I) in which B represents a CH(OH) grouping is required, the keto derivative obtained by reaction variant (a) or (b), of the general formula

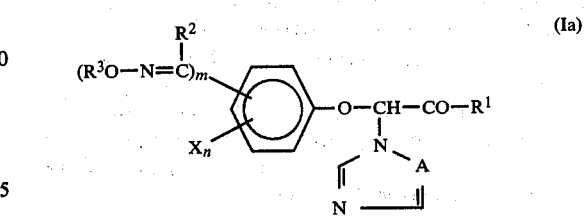

in which $R^1$, $R^2$, $R^3$, A, X, m and n have the meanings given above, is reduced; and, if desired, the compound obtained by reaction variant (a), (b) or (c) is converted into the acid addition salt or metal salt complex thereof.

The new compounds of the present invention exhibit powerful fungicidal properties. In this respect, the compounds according to the invention surprisingly exhibit a greater action than the 3,3-dimethyl-1-(imidazol-1-yl)- or (1,2,4-triazol-1-yl)-1-phenoxy-butan-2-ones and -oles substituted in the phenyl part, which are known from the prior art and are very similar compounds chemically and with respect to their action. The compounds according to the invention thus represent an enrichment of the art.

Preferred substituted azolyl-phenoxy derivatives according to the invention are those, in which $R^1$ represents a straight-chain or branched alkyl group having 1 to 4 carbon atoms, a straight-chain or branched halogenoalkyl group having 1 to 4 carbon atoms and 1 to 3 halogen atoms (preferably fluorine, chlorine or bromine atoms) or an optionally substituted phenyl group (the substituents thereon preferably being selected from halogen, alkyl having 1 to 4 carbon atoms, alkoxy and alylthio, each having 1 or 2 carbon atoms, and halogenoalkyl having 1 or 2 carbon atoms and 1 to 5 identical or different halogen atoms-such as fluorine atoms and chlorine atoms), $R^2$ represents a hydrogen atom, a straight-chain or branched alkyl group having 1 to 4 carbon atoms or an optionally substituted phenyl group (the substituents thereon preferably being selected from those mentioned as phenyl substituents under $R^1$), $R^3$ represents a hydrogen atom, a straight-chain or branched alkyl group having 1 to 4 carbon atoms or an alkenyl and alkinyl group, each having 2 to 4 carbon atoms;

X represents a halogen atom, a straight-chain or branched alkyl, alkoxy or alkylthio group, each having 1 to 4 carbon atoms or a halogenoalkyl, halogenoalkoxy or halogenoalkylthio group, each having 1 or 2 carbon atoms and 1 to 5 identical or different halogen atoms (such as fluorine atoms and chlorine atoms), A, B, m and n have the abovementioned meanings.

Particularly preferred compounds of the present invention are those, in which $R^1$ represents a tert.-butyl, chloro-tert.-butyl, fluoro-tert.-butyl, dichloro-tert.-butyl or difluorotert.-butyl group or a phenyl group which is optionally monosubstituted or disubstituted by identical or different substituents selected from fluorine, chlorine and methyl;

$R^2$ represents a hydrogen atom, a methyl, ethyl or isopropyl group or a phenyl group which is optionally monosubstituted or disubstituted by identical or different substituents selected from fluorine, chlorine, methyl, methoxy and trifluoromethyl;

$R^3$ represents a hydrogen atom or a methyl, ethyl, n-propyl, n-butyl, allyl or propargyl group, X represents a fluorine, chlorine, bromine or iodine atom or a methyl, methoxy, methylthio, trifluoromethyl, trifluoromethoxy or trifluoromethylthio group, and A, B, m and n have the meanings given above.

In addition to the compounds mentioned in the preparative examples, the following compounds of the general formula (I) may be mentioned individually:

TABLE 1

(Ib)

$R^3O-N=C(R^2)-\text{C}_6H_4-O-CH(B-R^1)-N\cdots A$ (triazole ring)

| $R^1$ | $R^2$ | $R^3$ | A | B |
|---|---|---|---|---|
| 2,4-Cl$_2$-C$_6$H$_3$- | H | CH$_3$ | CH | CO |
| 2,4-Cl$_2$-C$_6$H$_3$- | H | CH$_3$ | N | CO |
| 2,4-Cl$_2$-C$_6$H$_3$- | H | CH$_3$ | CH | CHOH |
| 2,4-Cl$_2$-C$_6$H$_3$- | H | CH$_3$ | N | CHOH |
| FCH$_2$-C(CH$_3$)$_2$- | H | CH$_3$ | CH | CO |
| FCH$_2$-C(CH$_3$)$_2$- | H | CH$_3$ | N | CO |
| FCH$_2$-C(CH$_3$)$_2$- | H | CH$_3$ | CH | CHOH |
| FCH$_2$-C(CH$_3$)$_2$- | H | CH$_3$ | N | CHOH |
| CH$_3$-C(CH$_2$F)$_2$- | H | CH$_3$ | CH | CO |
| CH$_3$-C(CH$_2$F)$_2$- | H | CH$_3$ | N | CO |
| CH$_3$-C(CH$_2$F)$_2$- | H | CH$_3$ | CH | CHOH |
| CH$_3$-C(CH$_2$F)$_2$- | H | CH$_3$ | N | CHOH |
| (CH$_3$)$_3$C- | C$_6$H$_5$ | CH$_3$ | CH | CO |
| (CH$_3$)$_3$C- | C$_6$H$_5$ | CH$_3$ | N | CO |
| (CH$_3$)$_3$C- | C$_6$H$_5$ | CH$_3$ | CH | CHOH |
| (CH$_3$)$_3$C- | C$_6$H$_5$ | CH$_3$ | N | CHOH |

If, for example, 1-bromo-3,3-dimethyl-1-(4-methoximinomethylphenoxy)-butan-2-one and 1,2,4-triazole are used as starting materials, the course of the reaction variant (a) according to the present invention is illustrated by the following equation:

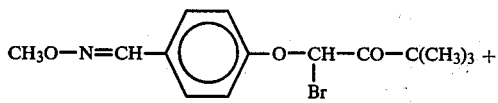

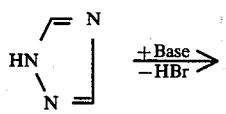

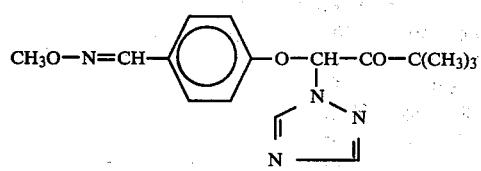

If, for example, 1-bromo-3,3-dimethyl-1-(1,2,4-triazol-1-yl)-butan-2-one and 2-hydroxy-benzaldehyde oxime O-methyl ether are used as starting materials the course of the reaction variant (b) according to the present invention is illustrated by the following equation:

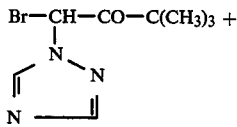

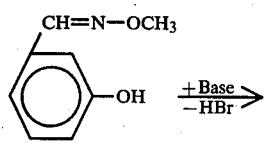

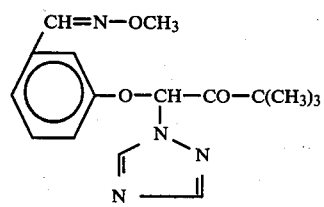

If, for example, 3,3-dimethyl-1-(4-methoximinomethylphenoxy)-1-(1,2,4-triazol-1-yl)-butan-2-one and sodium borohydride are used as starting materials the course of the reduction of reaction variant (c) according to the present invention is illustrated by the following equation:

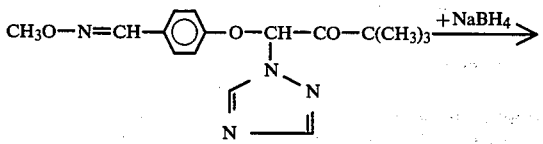

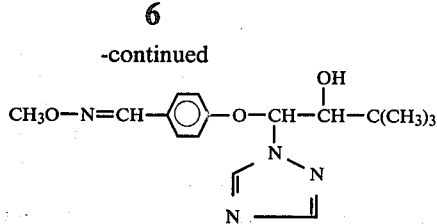

Preferred halogenoether-ketones of formula (II) to be used as starting materials in carrying out reaction variant (a) according to the invention are those in which $R^1$, $R^2$, $R^3$, X, m and n have those meanings which have already been mentioned in connection with the description of the preferred and particularly preferred compounds according to the invention and Hal represents a fluorine, chlorine or bromine atom.

The halogenoether-ketones of the formula (II) are novel. However, they can be obtained by known processes when a phenol of the general formula

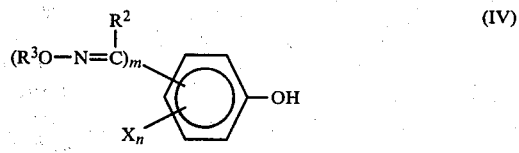

in which
$R^2$, $R^3$, X and n have the meanings given above, is reacted with a halogenoketone of the general formula

or

in which
Hal' represents a chlorine or bromine atom, and
$R^1$ has the meaning given above,
in the presence of an inert organic solvent (such as acetone) and in the presence of an acid-binding agent (such as potassium carbonate). When a halogenoketone of the formula (Va) is used, the remaining active hydrogen atom is subsequently replaced in the customary manner by chlorine or bromine.

The Phenols of the formula (IV) are known and can be obtained in a generally customary manner (see also the preparative examples hereinbelow).

Halogenoketones of the formulae (Va and Vb) are known (see, for example, U.S. Pat. Nos. 3,912,752 and 3,898,341, and U.S. application Ser. No. 182,357, filed Aug. 29, 1980, abandoned), and they can be obtained in a generally known manner. The halogenoketones of the formula (Va) are obtained by adding chlorine or bromine to the corresponding ketones, in the presence of an inert organic solvent (such as ethers or chlorinated hydrocarbons) at room temperature, or by reacting these ketones with customary chlorinating agents (such as sulphuryl chloride) at from 20° to 60° C. The halogenoketones of the formula (Vb) are obtained when the bromine or chlorine in the halogenoketones of the formula (Va) is replaced by fluorine in a customary manner, and one of the two active hydrogen atoms in the resulting corresponding fluoroketones is replaced by bromine or chlorine in the abovementioned manner.

Preferred azolylhalogenoketones of formula (III) to be used as starting materials in carrying out reaction variant (b) according to the invention are those in which $R^1$ and A have those meanings which have already been mentioned in connection with these radicals in the description of the preferred and particularly preferred compounds according to the present invention, and Hal' represents a fluorine, chlorine or bromine atom.

Azolylhalogenoketones of the formula (III) are known (see U.S. application Ser. No. 964,768, filed Nov. 29, 1978, now U.S. Pat. No. 4,396,624, and U.S. application Ser. No. 182,357, filed Aug. 29, 1980, abandoned), and they can be obtained according to the processes given in these references, for example by a process in which an azolylketone of the general formula

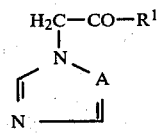

(VI)

in which A and $R^1$ have the meanings given above, is reacted with bromine or chlorine in the presence of an acidic solvent and, if appropriate, in the presence of a hydrogen halide acceptor, and, if appropriate, the bromine or chlorine in the corresponding azolyl-bromo- or -chloroketones is replaced by fluorine in a customary manner. The resulting azolylhalogenoketones can be directly reacted further, without isolation.

Azolylketones of the formula (VI) are known (see German Published Specification DOS No. 3,638,470, U.S. Application Ser. No. 291,699, filed Aug. 10, 1981, pending, U.S. application Ser. No. 182,380, filed Aug. 29, 1980), now U.S. Pat. No. 4,344,953 and they can be obtained according to the processes given in these references, by reacting a halogenoketone of the general formula

 (VII)

in which $R^1$ has the meaning given above, with 1,2,4-triazole or imidazole in the presence of a diluent (such as acetone) and in the presence of an acid-binding agent (such as potassium carbonate) at a temperature between 20° and 150° C.

Inert organic solvents are suitable diluents for the reaction variant (a) according to the present invention. These include, as preferences, ketones (such as diethyl ketone and, especially, acetone and methyl ethyl ketone), nitriles (such as propionitrile and, especially, acetonitrile), alcohols (such as ethanol or isopropanol), ethers (such as tetrahydrofuran or dioxane), benzene, toluene, formamides (such as, especially, dimethylformamide) and halogenated hydrocarbons.

The reaction variant (a) according to the invention is carried out, if appropriate, in the presence of an acid-binding agent. Any of the customarily usable inorganic or organic acid-binding agents can be added such as alkali metal carbonates (for example sodium carbonate, potassium carbonate and sodium bicarbonate) or such as lower tertiary alkylamines, cycloalkylamines or aralkylamines (for example triethylamine, N,N-dimethylcyclohexylamine, dicyclohexylamine, N,N-dimethylbenzylamine), and furthermore pyridine and diazabicyclooctane. An appropriate excess of triazole or imidazole is preferably used.

In reaction variant (a), the reaction temperatures can be varied within a relatively wide range. The reaction is carried out in general at a temperature between 20° and 150° C., preferably between 20° and 120° C. When a solvent is present, the reaction is advantageously carried out at the boiling point of the particular solvent.

In carrying out reaction variant (a) according to the invention, 2 mols of triazole or imidazole and from 1 to 2 mols of an acid-binding agent are preferably employed per mol of the compound of the formula (II). To isolate the compound of the formula (I), the solvent is generally distilled off, the residue taken up with an organic solvent, and the solution washed with water. The organic phase is generally dried over sodium sulphate and freed from the solvent in vacuo. The residue is purified by distillation or recrystallization, or salt formation and recrystallization.

In a preferred embodiment of reaction variant (a) according to the invention, compounds of the formula (II) in which Hal represents a fluorine atom are reacted directly in the form of a melt, at a temperature between 100° and 200° C., with 1,2,4-triazole or imidazole.

In a further preferred embodiment of reaction variant (a) according to the invention, compounds of the formula (I) in which B represents the CH(OH) grouping are obtained by first reducing, under the conditions given for reaction variant (c), a halogenoether-ketone of the formula (II) in which Hal represents a fluorine atom, and then reacting the product, according to the invention, with 1,2,4-triazole or imidazole.

Inert organic solvents are preferred diluents for reaction variant (b) according to the present invention. These include, as preferences, ethers (such as diethyl ether), alcohols (such as methanol), ketones (such as acetone), aromatic hydrocarbons (such as benzene) and also dimethylsulphoxide and dimethylformamide.

The reaction variant (b) according to the invention is carried out in the presence of an acid-binding agent. Any of the customarily usable inorganic or organic acid-binding agents can be added, such as alkali metal carbonates (for example potassium carbonate or sodium carbonate), alkali metal hydroxides (for example sodium hydroxide), or alkali metal alcoholates, or such as lower tertiary alkylamines (for example triethylamine).

In carrying out reaction variant (b) according to the invention, the reaction temperatures can be varied within a relatively wide range. The reaction is carried out in general at a temperature between 0° and 140° C., preferably between 50° and 100° C.

In carrying out reaction variant (b) according to the invention, from 1 to 4 mols of phenol of the formula (IV) are preferably employed per mol of the compound of the formula (III). The isolation of the compounds of the formula (I) is effected in the customary manner. The compounds of the formula (III) are preferably employed in the form of their hydrohalides.

The reduction according to the invention, according to process (c), is effected in the customary manner, for example, by reaction with complex hydrides, if appropriate in the presence of a diluent, or by reaction with aluminum isopropylate in the presence of a diluent.

If the reaction is carried out using complex hydrides, suitable diluents for the reaction according to the invention are polar organic solvents. These include, as preferences, alcohols (such as methanol, ethanol, butanol or isopropanol) and ethers (such as diethyl ether or tetrahydrofuran). The reaction is carried out in general at a temperature between 0° and 30° C., preferably between 0° and 20° C. For this purpose, about 1 mol of a complex hydride, such as sodium borohydride or lithium alanate, is employed per mol of the ketone of the formula (Ia). To isolate the reduced compounds of the formula (I), the residue is generally taken up in dilute hydrochloric acid, and the solution is then rendered alkaline and extracted with an organic solvent. Further working-up is effected in the customary manner.

If the reaction is carried out using aluminum isopropylate, preferred diluents for the reaction according to the invention are alcohols (such as isopropanol) or inert hydrocarbons (such as benzene). The reaction temperatures can again be varied within a relatively wide range, and the reaction is carried out in general at a temperature between 20° and 120° C., preferably between 50° and 100° C. To carry out the reaction, about 0.3 to 2 mol of aluminum isopropylate are employed per mol of the ketone of the formula (Ia). To isolate the reduced compounds of the formula (I), the excess solvent is removed in vacuo and the resulting aluminum compounds are decomposed with dilute sulphuric acid or sodium hydroxide solution. Further working-up is effected in the customary manner.

The following acids are preferred for the preparation of physiologically tolerated acid addition salts of the compounds of the formula (I): hydrohalic acids (such as hydrobromic acid and, preferably,hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid) and sulphonic acids (such as p-toluenesulphonic acid and naphthalene-1,5-disulphonic acid).

The acid addition salts of the compounds of the formula (I) can be obtained in a simple manner according to customary methods of salt formation, for example by dissolving a compound of the formula (I) in a suitable inert solvent and adding the acid (for example hydrochloric acid) and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), and copper, zinc, manganese, magnesium, tin, iron and nickel may be mentioned as examples. Suitable anions of the salts are those which are preferably derived from the following acids: hydrohalic acids (such as hydrochloric acid and hydrobromic acid), phosphoric acid, nitric acid and sulphuric acid.

The metal salt complexes of the compounds of the formula (I) can be obtained in a simple manner by customary processes, thus, for example, by dissolving the metal salt in alcohol (for example ethanol) and adding the solution to the compounds of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as against powdery mildew of barley (*Erysiphe graminis*) and stripe diseases of barley (*Drechslera graminea* and *Pyrenophora teres*), and also for combating rust diseases, such as against the bean rust causative organism (*Uromyces appendiculatus*), and scab diseases, such as against the apple scab causative organism (*Venturia inaequalis*). In addition, the active compounds according to the invention can also be used with good success against other plant diseases which are caused, for example, by the causative organisms of the fungus genera Puccinia, Leptosphaeria, Cochliobolus and Pyrenophora. The active compounds according to the invention also exhibit a good, broad in vitro spectrum.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02% by weight, are generally required at the place of action.

The present invention also provides fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

(a) Preparation of the starting material

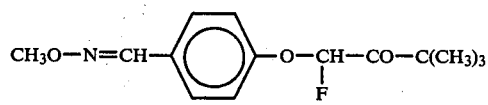

217 g (1.1 mol) of 1-bromo-1-fluoro-3,3-dimethyl-butan-2-one were added dropwise to a mixture of 151 g (1 mol) of 4-hydroxy-benzaldehyde oxime O-methyl ether and 154 g (1.1 mol) of finely powdered potassium carbonate in acetone, while stirring. After the slightly exothermic reaction had ended, the mixture was further stirred for another 3 hours. After the inorganic precipitate had been filtered off, the solution was concentrated and the residue was distilled in vacuo. 229 g (78% of theory) of 3,3-dimethyl-1-fluoro-1-(4-methoximinomethyl-phenoxy)-butan-2-one of boiling point 155° C./0.1 mm Hg were obtained.

(b)

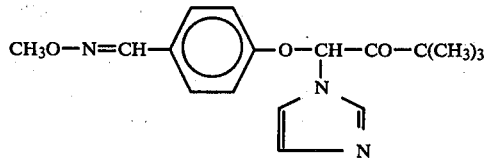

(Reaction variant (a))

220 g (0.82 mol) of 3,3-dimethyl-1-fluoro-1-(4-methoximinomethyl-phenoxy)-butan-2-one were added dropwise, while stirring, to a melt of 68 g (1 mol) of imidazole maintained at 150° C. The reaction mixture was further stirred for 3 hours at 150° C. and then introduced onto water, and the aqueous phase was extracted several times by shaking with methylene chloride. After the organic phase had been dried over sodium sulphate, the solvent was removed in vacuo. A dark oil remained, which crystallized through completely after some time. 210 g (82% of theory) of 3,3-dimethyl-1-(imidazol-1-yl)-1-(4-methoximinomethyl-phenoxy)-butan-2-one of melting point 73° to 80° C. were obtained.

EXAMPLE 2

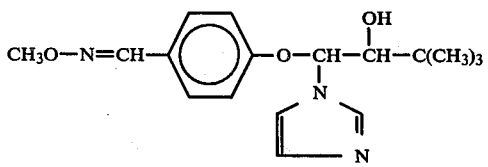

(Reaction variant (c))

5.65 g (0.018 mol) of 3,3-dimethyl-1-(imidazol-1-yl)-1-(4-methoximinomethyl-phenoxy)-butan-2-one (prepared as described in Example 1) were dissolved in methanol, and 2.3 g (0.06 mol) of sodium borohydride were added in portions at room temperature. The reaction mixture was stirred for 6 hours at room temperature, then poured onto water, and extracted with methylene chloride. The methylene chloride phase was dried over sodium sulphate and then concentrated. 4.1 g (72% of theory) of 3,3-dimethyl-1-(imidazol-1-yl)-1-(4-methoximinomethyl-phenoxy)-butan-2-ol of melting point 37° to 45° C. were obtained.

EXAMPLE 3

(a) Preparation of the starting material

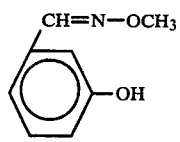

A mixture of 24.4 g (0.2 mol) of 3-hydroxy-benzaldehyde, 18.4 g (0.22 mol) of O-methylhydroxylamine hydrochloride and 22.2 g (0.22 mol) of triethylamine in 200 ml of ethanol was heated under reflux for 4 hours. After the solvent had been evaporated off, the residue was partitioned between water and methylene chloride, and the organic phase was dried over sodium sulphate and concentrated. 23.1 g (77% of theory) of 3-hydroxy-benzaldehyde oxime O-methyl ether of melting point 50° to 56° C. were obtained.

(b)

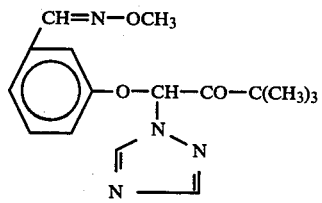

(Reaction variant (b))

10 g (0.06 mol) of 3,3-dimethyl-1-(1,2,4-triazol-1-yl)-butan-2-one and 4.9 g (0.06 mol) of sodium acetate in 100 ml of glacial acetic acid were initially introduced, and 9.6 g (0.06 mol) of bromine were added dropwise at 30° to 35° C., while stirring. Stirring was continued for 4 hours until the bromine coloration had completely disappeared; the reaction mixture was then poured onto water and extracted by shaking with chloroform. The chloroform phase was neutralized with sodium bicarbonate and concentrated in vacuo. The crude 1-bromo-(1,2,4-triazol-1-yl)-3,3-dimethyl-butan-2-one was added dropwise to a stirred mixture of 5.5 g (0.036 mol) of 3-hydroxy-benzaldehyde oxime O-methyl ether and 8.35 g (0.06 mol) of potassium carbonate at room temperature. After the slightly exothermic reaction had ceased, the mixture was stirred for 3 hours at room temperature, the precipitate was then filtered off under suction, and the solution was freed from the solvent in vacuo. The residue crystallized after trituration with petroleum ether. 11.25 g (98% of theory) of 3,3-dimethyl-1-(3-methoximinomethyl-phenoxy)-1-(1,2,4-triazol-1-yl)-butan-2-one of melting point 89° to 95° C. were obtained.

The compounds of the general formula (I)

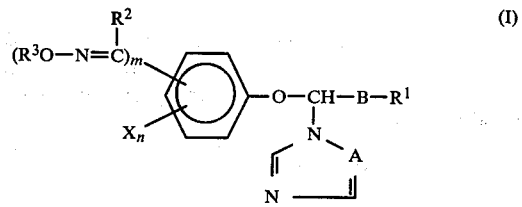

listed in the table below were obtained in an analogous manner and according to the processes according to the invention;

TABLE 2

| Compound No. | $R^2$<br>$(R^3O-N=C-)_m$ | $X_n$ | A | B | $R^1$ | Melting point (°C.) |
| --- | --- | --- | --- | --- | --- | --- |
| 4 | 4-CH=N—OCH$_3$ | — | N | CO | C(CH$_3$)$_3$ | viscous oil |
| 5 | 2-CH=N—OCH$_3$ | 4,6-Cl$_2$ | N | CO | C(CH$_3$)$_3$ | 93–98 |
| 6 | 3-CH=N—OCH$_3$ | 5-OCH$_3$ | N | CO | C(CH$_3$)$_3$ | 91–96 |
| 7 | 4-C=N—OCH$_3$<br>\|<br>CH$_3$ | — | N | CO | C(CH$_3$)$_3$ | 83–90 |
| 8 | 2-CH=N—OCH$_3$ | 4-Br | N | CO | C(CH$_3$)$_3$ | 131–37 |
| 9 | 2-CH=N—OCH$_3$ | — | N | CO | C(CH$_3$)$_3$ | 55–67 |
| 10 | 4-CH=N—OCH$_3$ | 2-OCH$_3$ | N | CO | C(CH$_3$)$_3$ | 93–110 |
| 11 | 4-CH=N—OCH$_3$ | — | N | CH(OH) | C(CH$_3$)$_3$ | viscous oil |
| 12 | 2-CH=N—OCH$_3$ | 4,6-Cl$_2$ | N | CH(OH) | C(CH$_3$)$_3$ | 105–24 |
| 13 | 3-CH=N—OCH$_3$ | 5-OCH$_3$ | N | CH(OH) | C(CH$_3$)$_3$ | viscous oil |
| 14 | 2-CH=N—OCH$_3$ | 4-Br | N | CH(OH) | C(CH$_3$)$_3$ | 52–70 |
| 15 | 4-C=N—OCH$_3$<br>\|<br>CH$_3$ | — | N | CH(OH) | C(CH$_3$)$_3$ | 121–36 |
| 16 | 2-CH=N—OCH$_3$ | — | N | CH(OH) | C(CH$_3$)$_3$ | 105–41 |
| 17 | 3-CH=N—OCH$_3$ | — | N | CH(OH) | C(CH$_3$)$_3$ | viscous oil |
| 18 | 4-CH=N—OCH$_3$ | 2-OCH$_3$ | N | CH(OH) | C(CH$_3$)$_3$ | 111–40 |
| 19 | 3-CH=N—OCH$_3$ | — | CH | CO | C(CH$_3$)$_3$ | viscous oil |

TABLE 2-continued

| Compound No. | $(R^3O-N=\overset{R^2}{\underset{|}{C}}-)_m$ | $X_n$ | A | B | $R^1$ | Melting point (°C.) |
|---|---|---|---|---|---|---|
| 20 | 3-CH=N—OCH₃ | — | CH | CH(OH) | C(CH₃)₃ | viscous oil |
| 21 | 4-C(=N—OCH₃)(C₆H₅) | — | N | CO | C(CH₃)₃ | 88–92° C. |
| 22 | 4-C(=N—OCH₃)(C₆H₅) | — | CH | CO | C(CH₃)₃ | $n_D^{20}$: 1.5542 |
| 23 | 4-CH=N—OCH₃ | — | N | CO | 3,4-Cl₂C₆H₃ | viscous oil |
| 24 | 4-C(=N—OCH₃)(CH₃) | — | N | CO | 3,4-Cl₂C₆H₃ | viscous oil |
| 25 | 4-CH=N—OCH₃ | 2-OCH₃ | N | CO | 3,4-Cl₂C₆H₃ | viscous oil |
| 26 | 4-C(=N—OCH₃)(C₆H₅) | — | N | CH(OH) | C(CH₃)₃ | resin |
| 27 | 4-C(=N—OCH₃)(CH₃) | — | CH | CO | C(CH₃)₃ | $n_D^{20}$: 1.5421 |
| 28 | 4-CH=N—OCH₃ | — | N | CH(OH) | 3,4-Cl₂C₆H₃ | 50–55 |
| 29 | 4-CH=N—OCH₃ | 2-OCH₃ | N | CH(OH) | 3,4-Cl₂C₆H₃ | 53–54 |
| 30 | 4-CH=N—OC₂H₅ | — | N | CO | C(CH₃)₃ | viscous oil |
| 31 | 4-CH=N—OC₂H₅ | — | N | CH(OH) | C(CH₃)₃ | 93–96 |
| 32 | 4-CH=N—OC₂H₅ | — | CH | CO | C(CH₃)₃ | viscous oil |

The fungicidal activity of the compounds of this invention is illustrated by the following biotest examples.

In these examples, the compounds according to the present invention are each identified by the number (given in brackets) from Examples 1 to 3 and Table 2.

The known comparison compounds are identified as follows:

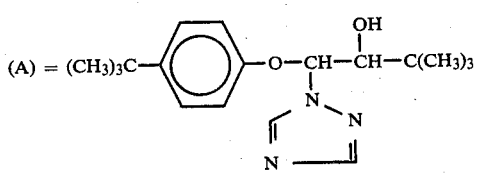

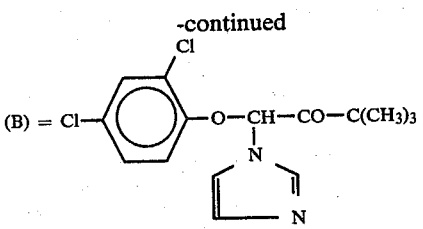

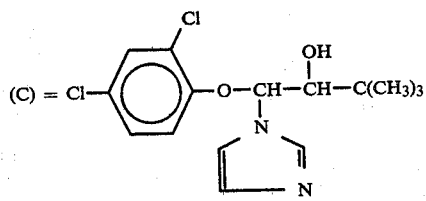

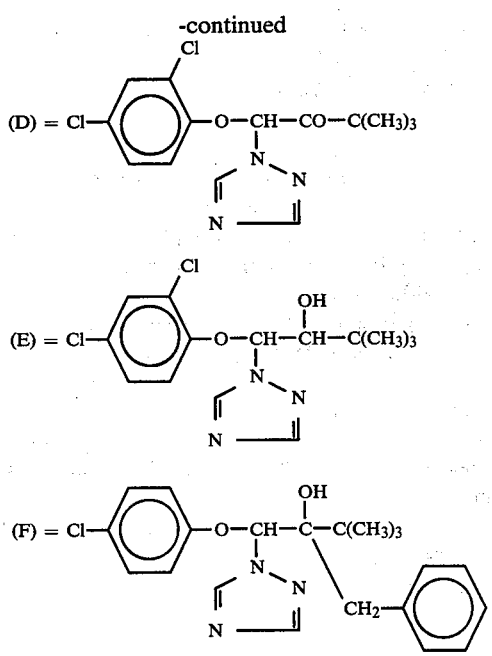

EXAMPLE 4

Erysiphe test (barley)/seed treatment

The active compounds were used as dry dressings. These were prepared by extending the particular active compound with a ground mineral to give a finely pulverulent mixture, which ensured uniform distribution on the seed surface.

To apply the dressing, the seed was shaken with the dressing in a closed glass flask for 3 minutes.

3 batches of 12 grains of the barley were sown 2 cm deep in standard soil. 7 days after sowing, when the young plants had unfolded their first leaf, they were dusted with spores of Erysiphe graminis f. sp. hordei.

The plants were placed in a greenhouse at a temperature of about 20° C. and a relative atmospheric humidity of about 80% in order to promote the development of powdery mildew pustules.

Evaluation was carried out 7 days after the inoculation.

In this test, a clearly superior activity compared with the prior art was shown, for example, by the compounds (2) and (11).

EXAMPLE 5

Drechslera graminea test (barley)/seed treatment (syn. Helminthosporium gramineum)

The active compounds were used as dry dressings. These were prepared by extending the particular active compound with a ground mineral to give a finely pulverulent mixture, which ensured uniform distribution on the seed surface.

To apply the dressing, the infected seed was shaken with the dressing in a closed glass flask for 3 minutes.

The seed was embedded in sieved, moist standard soil and was exposed to a temperature of 4° C. in closed Petri dishes in a refrigerator for 10 days. Germination of the barley, and possibly also of the fungus spores, was thereby initiated. 2 batches of 50 grains of the pregerminated barley were subsequently sown 3 cm deep in standard soil and were cultivated in a greenhouse at a temperature of about 18° C., in seedboxes which were exposed to light for 15 hours daily.

About 3 weeks after sowing, the plants were evaluated for symptoms of stripe disease.

In this test, a clearly superior activity compared with the prior art was shown, for example, by the compound (1).

EXAMPLE 6

Pyrenophora teres test (barley)/protective

Solvent: 100 parts by weight of dimethylformamide
Emulsifier: 0.25 part by weight of alkylarylpolyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dewmoist. After the spray coating had dried on, the plants were sprayed with a conidia suspension of Pyrenophora teres. The plants then remained in an incubation cabinet at 20° C. and 100% relative atmospheric humidity for 48 hours.

The plants were placed in a greenhouse at a temperature of about 20° C. and a relative atmospheric humidity of about 80%.

Evaluation was carried out 7 days after the inoculation.

In this test, a clearly superior activity compared with the prior art was shown, for example, by the compounds (1), (4), (2) and (11 ).

EXAMPLE 7

Uromyces test (dwarf bean)/protective

Solvent: 4.7 parts by weight of acetone
Emulsifier: 0.3 part by weight of alkylarylpolyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were inoculated with an aqueous uredospore suspension of the bean rust causative organism (Uromyces appendiculatus) and remained in a dark humidity chamber at 20° to 22° C. and 100% relative atmospheric humidity for 1 day.

The plants were then placed in a greenhouse under intensive illumination at 20° to b 22° C. and a relative atmospheric humidity of 70 to 80% for 9 days.

Evaluation was carried out 10 days after the inoculation.

In this test, a clearly superior activity compared with the prior art was shown, for example, by the compounds (4), (2) and (11).

EXAMPLE 8

Venturia test (apple)/protective

Solvent: 4.7 parts by weight of acetone
Emulsifier: 0.3 part by weight of alkylarylpolyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were inoculated with an aqueous conidia suspension of the apple scab causative organism (*Venturia inaequalis*) and then remained in an incubation cabinet at 20° C. and 100% relative atmospheric humidity for 1 day.

The plants were then placed in a greenhouse at 20° C. and a relative atmospheric humidity of about 70%.

Evaluation was carried out 12 days after the inoculation.

In this test, a clearly superior activity compared with the prior art was shown, for example, by the compounds (1), (4), (2) and (11).

It will be appreciated that the instant specification and examples are set forth by way of illustration and not limitation, and that various modifications and changes may be made without departing from the spirit and scope of the present invention.

We claim:

1. A substituted azolyl-phenoxy derivative of the formula

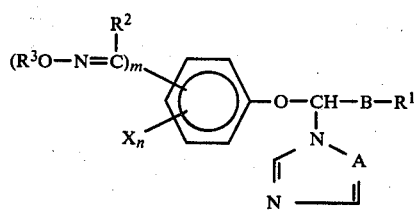

in which

A is a nitrogen atom or a CH group,

B is a keto group or a CH(OH) grouping, $R^1$ is an alkyl group having 1 to 4 carbon atoms, a halogenoalkyl group having 1 to 4 carbon atoms and 1 to 3 halogen atoms, or an optionally substituted phenyl group, $R^2$ is a hydrogen atom, an alkyl group having 1 to 4 carbon atoms, or an optionally substituted phenyl group, $R^3$ is a hydrogen atom, an alkyl group having 1 to 4 carbon atoms, or an alkenyl or alkinyl group each having 2 to 4 carbon atoms, the optional substituents on the phenyl group of $R^1$ and/or $R^2$ being selected from the group consisting of halogen, alkyl having 1 to 4 carbon atoms, alkoxy or alkylthio each having 1 or 2 carbon atoms, and halogenoalkyl having 1 or 2 carbon atoms and 1 to 5 halogen atoms, m is 1 or 2, X is a halogen atom, an alkyl, alkoxy or alkylthio group each having 1 to 4 carbon atoms, or a halogenoalkyl, halogenoalkoxy or halogenoalkylthio group each having 1 or 2 carbon atoms and 1 to 5 halogen atoms, and n is 0, 1 or 2, or an addition product thereof with an acid or metal salt.

2. A compound or addition product thereof according to claim 1, in which $R^1$ is a tert.-butyl, chloro-tert.-butyl, fluoro-tert.-butyl, dichloro-tert.-butyl or difluoro-tert.-butyl group, a phenyl group or a phenyl group substituted by fluorine, chlorine and/or methyl, $R^2$ is a hydrogen atom, a methyl, ethyl or isopropyl group, a phenyl group or a phenyl group substituted by fluorine, chlorine, methyl, methoxy and/or trifluoromethyl, $R^3$ is a hydrogen atom or a methyl, ethyl, n-propyl, n-butyl, allyl or propargyl group, and X is a fluorine, chlorine, bromine or iodine atom, or a methyl, methoxy, methylthio, trifluoromethyl, trifluoromethoxy or trifluoromethylthio group.

3. A compound according to claim 1, wherein such compound is 3,3-dimethyl-1-(imidazol-1-yl)-1-(4-methoximinomethyl-phenoxy)-butan-2-one of the formula

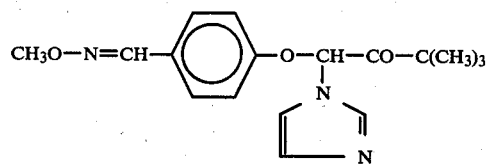

or an addition product thereof with an acid or metal salt.

4. A compound according to claim 1, wherein such compound is 3,3-dimethyl-1-(imidazol-1-yl)-1-(4-(4-methoximinomethyl-phenoxy)-butan-2-ol of the formula

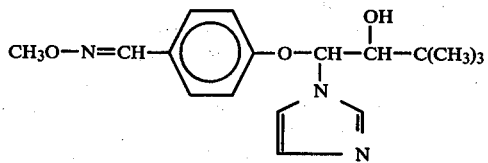

or an addition product thereof with an acid or metal salt.

5. A compound according to claim 1, wherein such compound is 3,3-dimethyl-1-(1,2,4-triazol-1-yl)-1-(4-methoximinomethyl-phenoxy)-butan-2-one of the formula

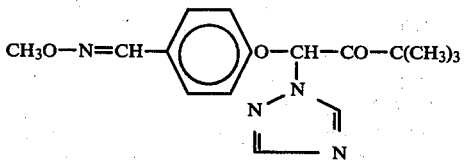

or an addition product thereof with an acid or metal salt.

6. A compound according to claim 1, wherein such compound is 3,3-dimethyl-1-(1,2,4-triazol-1-yl)-1-(4-(1-methoximinoethyl)-phenoxy)-butan-2-one of the formula

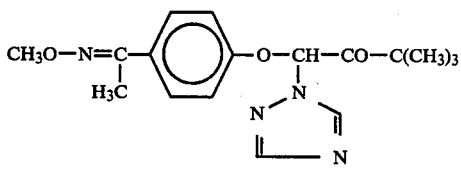

or an addition product thereof with an acid or metal salt.

7. A compound according to claim 1, wherein such compound is 3,3-dimethyl-1-(1,2,4-triazol-1-yl)-1-(4-methoximinomethyl-phenoxy)-butan-2-ol of the formula

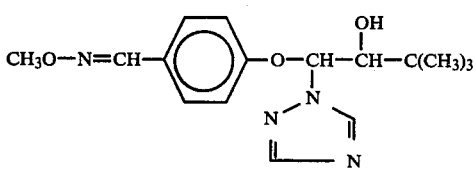

or an addition product thereof with an acid or metal salt.

8. A fungicidal composition comprising a fungicidally effective amount of a compound or addition product thereof according to claim 1 in admixture with a diluent.

9. A method of combating fungi comprising applying to the fungi, or to a habitat thereof, a fungicidally effective amount of a compound or addition product thereof according to claim 1.

10. The method according to claim 9, wherein such compound is
- 3,3-dimethyl-1-(imidazol-1-yl)-1-(4-methoximinomethyl-phenoxy)-butan-2-one,
- 3,3-dimethyl-1-(imidazol-1-yl)-1-(4-methoximinomethyl-phenoxy)-butan-2-ol,
- 3,3-dimethyl-1-(1,2,4-triazol-1-yl)-1-(4-methoximinomethyl-phenoxy)-butan-2-one,
- 3,3-dimethyl-1-(1,2,4-triazol-1-yl)-1-(1-methoximinoethyl)-butan-2-one, or
- 3,3-dimethyl-1-(1,2,4-triazol-1-yl)-1-(4-methoximinomethyl-phenoxy)-butan-2-ol, or an addition product thereof with an acid or metal salt.

* * * * *

UNITED STATES PATENT AND TRADEMARK OFFICE
CERTIFICATE OF CORRECTION

PATENT NO. : 4,472,416  Page 1 of 2

DATED : September 18, 1984

INVENTOR(S) : Jörg Stetter, et al

It is certified that error appears in the above-identified patent and that said Letters Patent is hereby corrected as shown below:

Abstract, line 12 Col. 1, line 40, Col. 2, line 2, Col. 2, line 31, Col. 2, line 48, Col. 3, lines 23 and 42, Col 6, line 12, Col 19, line 60     Delete "m" and substitute --$\underline{m}$--

Abstract, line 16, Col. 1, line 44, Col. 2, line 2, Col. 2, line 31, Col. 2, line 48, Col. 3, lines 23 and 42, Col. 6, lines 12 and 30, Col. 19, line 66     Delete "n" and substitute --$\underline{n}$--

Col. 4, line 12, under column "R'"     Delete formula and substitute --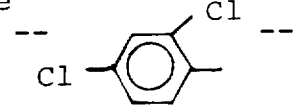--

UNITED STATES PATENT AND TRADEMARK OFFICE
CERTIFICATE OF CORRECTION

PATENT NO. : 4,472,416

DATED : September 18, 1984

INVENTOR(S) : Jörg Stetter, et al

It is certified that error appears in the above-identified patent and that said Letters Patent is hereby corrected as shown below:

Col. 7, line 31          Delete "3,638,470" and substitute --2,638,470--

Col. 20, line 35         After "-1-" delete "(4-" first instance

Col. 22, line 19         Delete "(1-methoxoimino-ethyl)-" and substitute --(4-(1-methoximino-ethyl)-phenoxy)- --

Signed and Sealed this

Sixteenth Day of April 1985

[SEAL]

Attest:

DONALD J. QUIGG

Attesting Officer

Acting Commissioner of Patents and Trademarks